United States Patent [19]
Hirohashi et al.

[11] 3,957,783
[45] *May 18, 1976

[54] THIENO[2,3-D]PYRIMIDINE DERIVATIVES

[75] Inventors: Toshiyuki Hirohashi, Ashiya; Hiromi Sato; Shigeho Inaba, both of Takarazuka; Hisao Yamamoto, Nishinomiya, all of Japan

[73] Assignee: Sumitomo Chemical Company, Limited, Osaka, Japan

[ * ] Notice: The portion of the term of this patent subsequent to May 18, 1993, has been disclaimed.

[22] Filed: May 7, 1973

[21] Appl. No.: 357,889

[30] Foreign Application Priority Data

| May 9, 1972 | Japan | 47-46038 |
| July 3, 1972 | Japan | 47-66828 |
| July 26, 1972 | Japan | 47-75420 |
| Dec. 9, 1972 | Japan | 47-12367 |
| Dec. 14, 1972 | Japan | 47-12594 |

[52] U.S. Cl. ............. 260/251 A; 260/256.4 F; 260/332.3 R; 260/256.5 R; 260/330.5; 260/247.2 A; 260/329 AM; 260/332.2 R; 424/251; 260/247.7 R; 260/247.7 V; 260/247.7 Z

[51] Int. Cl.² ............................... C07D 495/04
[58] Field of Search ......................... 260/251 A

[56] References Cited
UNITED STATES PATENTS
3,830,813   8/1974   Woitum et al. .......... 260/256.5 R

OTHER PUBLICATIONS

Robba et al., Chemical Abstracts, V. 70, 37,767b (1969).
Robba et al., Chemical Abstracts, V. 69, 27,365j (1968).
Robba et al., Chemical Abstracts, V. 69, 96,635j (1968).
Sauter, Chemical Abstracts, V. 69, 96,647q (1968).
Gronowitz et al., Chemical Abstracts, V. 70, 87,745p (1969).
Manhas et al., Chemical Abstracts, V. 71, 101,801h (1969).
Schweizer et al., Chemical Abstracts, V. 72, 90,498g (1970).
Manhas et al., Chemical Abstracts, V. 76, 107846b, (5/8/72).

*Primary Examiner*—Raymond V. Rush
*Assistant Examiner*—Diana G. Rivers
*Attorney, Agent, or Firm*—Stevens, Davis, Miller & Mosher

[57] ABSTRACT

Novel thienopyrimidine derivatives which have excellent pharmacological uricosuric activity are prepared by reacting a thiophene derivative with cyanic acid or a salt thereof, urea or a reactive ester of carbamic acid. If desired, alkylated, halogenated or nitrated thienopyrimidine derivatives are produced by reacting thienopyrimidine derivatives with an alkylating, halogenating or nitrating agent, respectively.

5 Claims, No Drawings

THIENO[2,3-D]PYRIMIDINE DERIVATIVES

This invention relates to novel thienopyrimidine derivatives and a process for production thereof. More particularly, the present invention relates to novel thienopyrimidine derivatives of the formula,

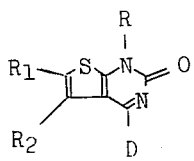

and their isomers of the formulae,

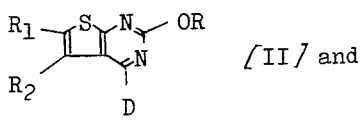

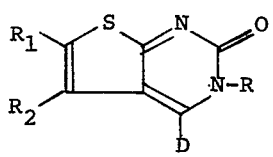

wherein D is a hydrogen atom, a lower alkyl group or a group of the formula,

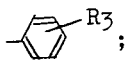

$R_1$ is a hydrogen atom, a lower alkyl group, a lower alkoxy group, a nitro group, a trifluoromethyl group, a lower alkylthio group, a lower alkylsulfonyl group, a halogen atom or $R_1$ and $R_2$ may together form a trimethylene, tetramethylene or pentamethylene group; $R_2$ and $R_3$ are independently a hydrogen atom, a lower alkyl group, a lower alkoxy group, a nitro group, a trifluoromethyl group, a lower alkylthio group, a lower alkylsulfonyl group or a halogen atom; R is a hydrogen atom, a lower alkyl group, a lower alkenyl group, an aralkyl group, a lower alkoxyalkyl group, a cycloalkylalkyl group, a lower haloalkyl group, a lower alkylthioalkyl group, a lower alkoxycarbonylalkyl group, a lower alkanoyloxyalkyl group, or a group of the formula,

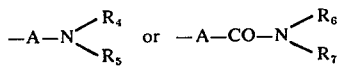

(wherein A is a lower alkylene group; $R_4$, $R_5$, $R_6$ and $R_7$ are independently a hydrogen atom or a lower alkyl group, which may form together with the adjacent nitrogen atom an unsubstituted or optionally substituted 5- or 6-membered heterocyclic ring, which may further contain a hetero atom, a process for production and pharmaceutical composition thereof.

In the compounds of the above formulae [I], [II], and [III], the term "halogen" includes all halogen atoms, i.e. fluorine, chlorine, bromine and iodine; the term "alkyl" means both straight and branched chain aliphatic hydrocarbon radicals, and lower alkyl is, for example, $C_{1-4}$ alkyl which includes such groups as methyl, ethyl, n-propyl, isopropyl, n-butyl, iso-butyl and tertiary-butyl; the term "lower alkoxy" is, for example, $C_{1-4}$ alkoxy which includes such groups as methoxy, ethoxy, n-propoxy, isopropoxy, n-butoxy and tertiary-butoxy; the term "lower alkylthio" is, for example, $C_{1-4}$ alkylthio which includes such groups as methylthio, ethylthio, propylthio, and butylthio; the term "lower alkylsulfonyl" is, for example, $C_{1-4}$ alkylsulfonyl which includes such groups as methylsulfonyl, ethylsulfonyl, propylsulfonyl, etc.; the term "lower alkenyl" is, for example, $C_{3-5}$ alkenyl which includes such groups as allyl, methallyl, 3-butenyl, crotyl, etc.; the term "aralkyl" is, for example, a benzyl, phenethyl, o-chlorobenzyl, p-chlorobenzyl, o-methylbenzyl or phenylpropyl group; the term "lower alkoxyalkyl" is, for example, ($C_{1-4}$ alkoxy)$C_{1-4}$ alkyl; the term "cycloalkylalkyl" is, for example, ($C_{3-6}$ cycloalkyl)$C_{1-4}$ alkyl in which the $C_{3-6}$ cycloalkyl moiety includes such groups as cyclopropyl, cyclobutyl, cyclohexyl, etc; the term "lower alkylthioalkyl" is, for example, ($C_{1-4}$ alkylthio)$C_{1-4}$ alkyl; the term "lower alkoxycarbonylalkyl" is, for example, ($C_{1-4}$ alkoxy)carbonyl ($C_{1-4}$ alkyl); the term "lower alkanoyloxyalkyl" is, for example, ($C_{2-3}$ alkanoyloxy)$C_{1-4}$ alkyl in which the $C_{2-3}$ alkanoyloxy moiety includes such groups as acetoxy and propionyloxy; the term "haloalkyl" is, for example, (halogen substituted)$C_{1-4}$ alkyl; the term "lower alkylene" is, for example, straight chain or branched chain $C_{1-4}$ alkylene which includes such groups as methylene, ethylene, 1-methylethylene, 2-methylethylene, trimethylene, 1-methyltrimethylene, 2-methyltrimethylene, etc.; the term "substituted or unsubstituted 5- or 6-membered heterocyclic ring" is, for example, a pyrrolidino, piperidino, or morpholino group or substituted derivatives thereof.

The thienopyrimidine derivatives of the formulae [I], [II] and [III], which have not been described in any literature, have excellent uricosuric activity, with low toxicities to mammals which render them useful as synthetic medicinals.

In accordance with the process of the present invention, a thienopyrimidine derivative of the formula [I] can be prepared by reacting a thiophene derivative of the formula.

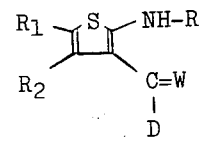

wherein $R_1$, $R_2$, D and R are as defined above; and W is an oxygen atom or an imino group, with a compound selected from the group consisting of cyanic acid or a salt thereof, urea and a reactive ester of carbamic acid, and if desired, a. reacting a thienopyrimidine derivative of the formula,

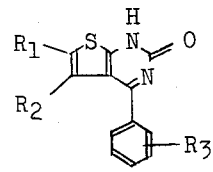

wherein $R_1$, $R_2$ and $R_3$ are as defined above, with a reative ester of a compound represented by the formula,

R''—OH  [V]

wherein R'' is the same as R except that it does not include a hydrogen atom and $R_4$ and $R_5$ do not include a hydrogen atom; to yield a thienopyrimidine derivative of the formula [I], [II] or [III], b. reacting a thienopyrimidine derivative of the formula,

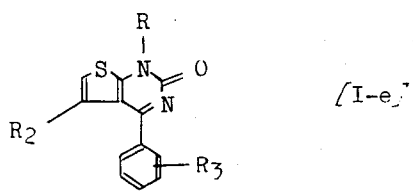 [I-e]

wherein $R_2$, $R_3$ and R are as defined above, with a halogenating agent to yield a thienopyrimidine derivative of the formula,

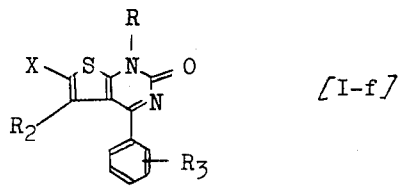 [I-f]

wherein $R_2$, $R_3$ and R are as defined above, and X is a halogen atom, or c. reacting a thienopyrimidine derivative of the formula,

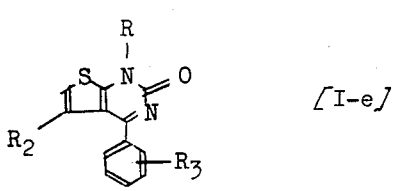 [I-e]

wherein $R_2$, $R_3$ and R are as defined above, with a nitrating agent to yield a thienopyrimidine derivative of the formula,

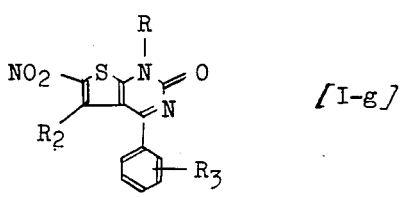 [I-g]

wherein $R_2$, $R_3$ and R are as defined above.

More precisely, a thienepyrimidne derivative of the formula,

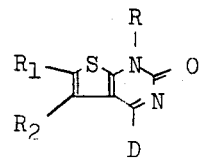 [I]

wherein $R_1$, $R_2$, R and D are as defined above, is prepared by reacting a compound of the formula,

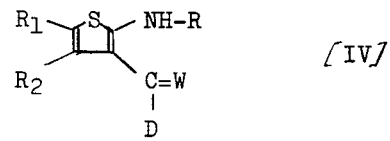 [IV]

wherein $R_1$, $R_2$, R and D are as defined above; and W is an oxygen atom or an imino group, with a compound selected from the group consisting of cyanic acid or a salt thereof, urea and a reactive ester of carbamic acid.

The reaction of the compound of the formula [IV] with cyanic acid or a salt thereof can be carried out in an acidic solvent such as acetic acid, formic acid or the like preferably at a temperature of from 50° to 100°C. As the salt of cyanic acid, sodium cyanate, potassium cyanate, and the like are preferable.

The reaction of the compound of the formula [IV] with urea can be carried out at 150° – 220°C preferably.

The reaction of the compound of the formula [IV] with a reactive ester of carbamic acid can be carried out at 150° – 220°C in the presence of a Lewis acid such as zinc chloride, aluminum chloride, boron trifluoride and the like. As the reactive ester of carbamic acid, carbamyl chloride, methyl carbamate, ethyl carbamate, benzyl carbamate, and the like are preferable.

According to the above mentioned process, the following theinopyrimidine derivatives, for example, can be obtained.

1-Methyl-4-(o-chlorophenyl)-1,2-dihydrothieno-[2,3-d]pyrimidin-2-one, m.p. 225° – 226°C.

1-Methyl-4-phenyl-1,2-dihydrothieno[2,3-d]-pyrimidin-2-one, m.p. 256° – 257.5°C.

1-Cyclopropylmethyl-4-phenyl-1,2-dihydrothieno[2,3-d]pyrimidin-2-one, m.p. 191° – 191.5°C.

1-Methyl-4-phenyl-6-chloro-1,2-dihydrothieno[2,3-d]pyrimidin-2-one, m.p. 136° – 140°C.

1-Cyclopropylmethyl-4-phenyl-6-chloro-1,2-dihydrothieno[2,3-d]pyrimidin-2-one, m.p. 149° – 151°C.

1-Methyl-4-(o-fluorophenyl)-6-chloro-1,2-dihydrothieno 2,3-d]pyrimidin-2-one, m.p. 192.5° – 194°C.

1-Methyl-4-phenyl-6-nitro-1,2-dihydrothieno[2,3-d]pyrimidin-2-one, m.p. 274 – 277°C.

1-Cyclopropylmethyl-4-phenyl-6-nitro-1,2-dihydrothieno[2,3-d]pyrimidin-2-one, m.p. 215° –218°C.

1-Methyl-4-(o-fluorophenyl)-5-methyl-1,2-dihydrothieno[2,3-d]pyrimidin-2-one

1-Methyl-4-(o-fluorophenyl)-6-methyl-1,2-dihydrothieno[2,3-d]pyrimidin-2-one

1-Methyl-4-(o-fluorophenyl)-1,2,5,6,7,8-hexahydrobenzothieno[2,3-d]pyrimidin-2-one 1-Benzyl-4-phenyl-1,2-dihydrothieno[2,3-d]-pyrimidin-2-one 1-(β-Ethoxyethyl)-4-phenyl-1,2-dihydrothieno[2,3-d]pyrimidin-2-one 1-(β-Acetoxyethyl)-4-phenyl-1,2-dihydrotheino[2,3-d]pyrimidin-2-one 1-Cyclohexylmethyl-4-phenyl-1,2,5,6,7,8-hexahydrobenzothieno[2,3-d]pyrimidin-2-one 1-(Methoxycarbonylmethyl)-4-phenyl-1,2-dihydrothieno[2,3-d]pyrimidin-2-one 1-(N-Methylcarbamoylmethyl)-4-phenyl-1,2-dihydrothieno[2,3-d]pyrimidin-2-one 1-(β-Methylthioethyl)-4-phenyl-1,2-dihydrothieno[2,3-d]pyrimidin-2-one 1-Allyl-4-phenyl-1,2-dihydrothieno[2,3-d]pyrimidin-2-one 1-(β-Diethylaminoethyl)-4-phenyl-1,2-dihydrothieno[2,3-d]pyrimidin-2-one 1-(β-Pyrrolydinoethyl)-4-phenyl-1,2-dihydrothieno[2,3-d]pyrimidin-2-one 1-(β-Morpholinoethyl)-4-phenyl-1,2-dihydrothieno[2,3-d]pyrimidin-2-one 1-(β-Piperidinoethyl)-4-phenyl-1,2-dihydrothieno[2,3-d]pyrimidin-2-one 1-Methyl-4-ethyl-5-methyl-1,2-dihydrothieno[2,3-d]pyrimidin-2-one 1-Methyl-4,6-diethyl-1,2dihydrothieno[2,3-d]pyrimidin-2-one 4-Ethyl-1,2-dihydrothieno[2,3-d]pyrimidin-2-one 1-Methyl-4-ethyl-1,2-dihydrothieno[2,3d]pyrimidin-2-one Further, if desired, a thienopyrimidine derivative of the formula,

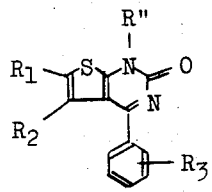

[I-d]

or

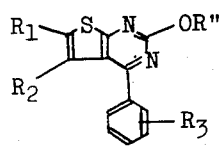

[II']

or

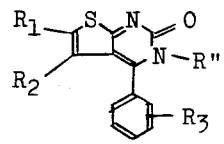

[III']

wherein $R_1$, $R_2$, $R_3$, and R'' are as defined above, is prepared by reacting a thienopyrimidine derivative of the formula,

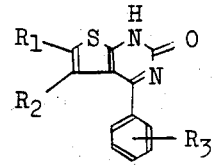

[I-c]

wherein $R_1$, $R_2$ and $R_3$ are as defined above, with a reactive ester of a compound represented by the formula,

R'' — OH    [V]

wherein R'' is as defined above, in the presence of a basic condensing agent in an inert organic solvent.

Examples of the reactive ester include, for example, hydrohalic acid esters such as chlorides, bromides and iodides and sulfonic acid esters such as methanesulfonate, p-toluenesulfonate, β-naphthalenesulfonate, trichloromethanesulfonate or the like.

As the basic condensing agent, sodium hydride, sodium methylate, sodium ethylate, sodium hydroxide, potassium carbonate, sodium amide, potassium amide, butyllithium, phenyllithium and the like are preferable.

As the inert organic solvent, benzene, toluene, xylene, dimethyl formamide, dimethyl acetamide, diphenyl ether, N-methyl pyrrolidone and the like are preferable.

The above-mentioned reaction can preferably be carried out at a temperature of from 0°C to the boiling point of the solvent employed. Needless to say, the reaction temperature may be varied with the alkylating agent used.

In the above-mentioned reaction, the thienopyrimidine derivatives of the formulae [I-d], [II'] and [III'] or the formulae [I-d] and [II'] are usually produced, but they can easily be separated by chromatography, recrystallization and the like.

According to the above-mentioned process, the following thienopyrimidine derivatives, for example, can be obtained.

1-Methyl-4-phenyl-6-chloro-1,2-dihydrothieno[2,3-d]pyrimidin-2-one

1-Cyclopropylmethyl-4-phenyl-6-chloro-1,2-dihydrothieno[2,3-d]pyrimidin-2-one

1-Methyl-4-(o-fluorophenyl)-6-chloro-1,2-dihydrothieno[2,3-d]pyrimidin-2-one

1-Methyl-4-phenyl-6-nitro-1,2-dihydrothieno[2,3-d]pyrimidin-2-one

1-Cyclopropylmethyl-4-phenyl-6-nitro-1,2-dihydrothieno[2,3-d]pyrimidin-2-one

1-Methyl-4-(o-fluorophenyl)-1,2,5,6,7,8-hexahydrobenzothieno[2,3-d]pyrimidin-2-one 1-Methyl-4-phenyl-1,2,5,6,7,8-hexahydrobenzothieno[2,3-d]pyrimidin-2-one 1-Benzyl-4-phenyl-1,2-dihydrothieno[2,3-d]-pyrimidin-2-one 1-(β-Ethoxyethyl)-4-phenyl-1,2-dihydrothieno[2,3-d]pyrimidin-2-one 1-(β-Acetoxyethyl)-4-phenyl-1,2-dihydrothieno[2,3-d]pyrimidin-2-one 1-(Methoxycarbonylmethyl)-4-phenyl-1,2-dihydrothieno[2,3-d]pyrimidin-2-one 1-(N-Methylcarbamoylmethyl)-4-phenyl-1,2-dihydrothieno[2,3-d]pyrimidin-2-one 1-(β-Methylthioethyl)-4-phenyl-1,2-dihydrothieno[2,3-d]pyrimidin-2-one 1-Allyl-4-phenyl-1,2-dihydrothieno[2,3-d]-pyrimidin-2-one 1-(β-Diethylaminoethyl)-4-phenyl-1,2-dihydrothieno[2,3-d]pyrimidin-2-one 1-(β-Pyrrolydinoethyl)-4-phenyl-1,2-dihydrothieno[2,3-d]pyrimidin-2-one 1-(β-Morpholinoethyl)-4-phenyl-1,2-dihydrothieno[2,3-d]pyrimidin-2-one 1-(β-Piperidinoethyl)-4-phenyl-1,2-dihydrothieno[2,3-d]pyrimidin-2-one Still further, if desired, a thienopyrimidine derivative of the formula,

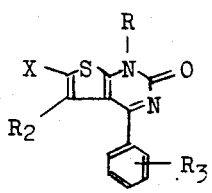

wherein R, $R_2$, $R_3$ and X are as defined above, is prepared by reacting a thienopyrimidine derivative of the formula,

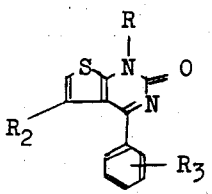

wherein R, $R_2$ and $R_3$ are as defined above, with a halogenating agent in the presence of an inert organic solvent.

As the halogenating agent, chlorine, sulfuryl chloride, bromine, iodine-mercuric oxide (yellow), N-bromosuccinimide, N-chlorosuccinimide, and the like are preferable.

As the inert organic solvent, halogenated carbons such as chloroform, carbon tetrachloride, dichloromethane, and the like; ethers such as ethyl ether, dioxane, and the like; organic acids such as acetic acid, formic acid, and the like; amines such as pyridine, triethylamine, and the like; aromatic hydrocarbons such as benzene, toluene, xylene and the like; or a mixture thereof are preferable.

The reaction mentioned above may be carried out at a temperature of from 0°C to the boiling point of a solvent used.

According to the above-mentioned process, the following thienopyrimidine derivatives, for example, can be obtained.

1-Methyl-4-phenyl-6-chloro-1,2-dihydrothieno[2,3-d]pyrimidin-2-one

4-Phenyl-6-chloro-1,2-dihydrothieno[2,3-d]-pyrimidin-2-one

1-Cyclopropylmethyl-4-phenyl-6-chloro-1,2-dihydrothieno[2,3-d]pyrimidin-2-one

1-Methyl-4-(o-fluorophenyl)-6-chloro-1,2-dihydrothieno[2,3-d]pyrimidin-2-one

1-Methyl-4-(o-chlorophenyl)-6-chloro-1,2-dihydrothieno[2,3-d]pyrimidin-2-one

1-Methyl-4-(o-tolyl)-6-chloro-1,2-dihydrothieno[2,3-d]pyrimidin-2-one

1-Methyl-4-(o-nitrophenyl)-6-chloro-1,2-dihydrothieno[2,3-d]pyrimidin-2-one

1-Methyl-4-phenyl-5-methyl-6-chloro-1,2-dihydrothieno[2,3-d]pyrimidin-2-one

1-Benzyl-4-phenyl-6-chloro-1,2-dihydrothieno[2,3-d]pyrimidin-2-one 1-(β-Ethoxyethyl)-4-phenyl-6-chloro-1,2-dihydrothieno[2,3-d]pyrimidin-2-one 1-(β-Acetoxyethyl)-4-phenyl-6-chloro-1,2-dihydrothieno[2,3-d]pyrimidin-2-one 1-(Methoxycarbonylmethyl)-4-phenyl-6-chloro-1,2-dihydrothieno[2,3-d]pyrimidin-2-one 1-(N-Methylcarbamoylmethyl)-4-phenyl-6-chloro-1,2-dihydrothieno[2,3-d]pyrimidin-2-one 1(Carbamoylethyl)-4-phenyl-6-chloro-1,2-dihydrothieno[2,3-d]pyrimidin-2-one 1-(β-Methylthioethyl)-4-phenyl-6-chloro-1,2-dihydrothieno[2,3-d]pyrimidin-2-one 1-Allyl-4-phenyl-6-chloro-1,2-dihydrothieno[2,3-d]pyrimidin-2-one 1-(β-Diethylaminoethyl)-4-phenyl-6-chloro-1,2-dihydrothieno[2,3-d]pyrimidin-2-one 1-(β-Pyrrolidinoethyl)-4-phenyl-6-chloro-1,2-dihydrothieno[2,3-d]pyrimidin-2-one 1-(β-Morpholinoethyl)-4-phenyl-6-chloro-1,2-dihydrothieno[2,3-d]pyrimidin-2-one 1-(β-Piperidinoethyl)-4-phenyl-6-chloro-1,2-dihydrothieno[2,3-d]pyrimidin-2-one Furthermore, if desired, a thienopyrimidine derivative of the formula,

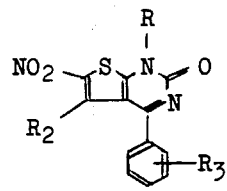

wherein R, $R_2$ and $R_3$ are as defined above, is prepared by reacting a thienopyrimidine derivative of the formula,

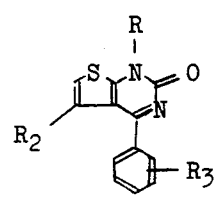

wherein R, R₂ and R₃ are as defined above, with a nitrating agent preferably in a solvent.

As the nitrating agent, nitric acid, fuming nitric acid, potassium nitrate and the like are preferable.

As the solvent, sulfuric acid, acetic acid, acetic anhydride, and the like are preferable.

The reaction mentioned above is preferably carried out at a temperature of from −10°C to 150°C.

According to the above-mentioned process, the following thienopyrimidine derivatives, for example, can be obtained.

1-Methyl-4-phenyl-6-nitro-1,2-dihydrothieno-[2,3-d]pyrimidin-2-one

4-Phenyl-6-nitro-1,2-dihydrothieno[2,3-d]-pyrimidin-2-one

1-Cyclopropylmethyl-4-phenyl-6-nitro-1,2-dihydrothieno[2,3-d]pyrimidin12-one

1-Methyl-4-(o-fluorophenyl)-6-nitro-1,2-dihydrothieno[2,3-d]pyrimidin-2-one

1-Methyl-4-(o-chlorophenyl)-6-nitro-1,2-dihydrothieno[2,3-d]pyrimidin-2-one

1-Methyl-4-(o-tolyl)-6-nitro-1,2-dihydrothieno[2,3-d]pyrimidin-2-one

1-Methyl-4-(o-nitrophenyl)-6-nitro-1,2-dihydrothieno[2,3-d]pyrimidin-2-one

1-Methyl-4-phenyl-5-methyl-6-nitro-1,2-dihydrothieno[2,3-d]pyrimidin-2-one

1-Benzyl-4-phenyl-6-nitro-1,2-dihydrothieno-[2,3-d]pyrimidin-2-one 1-(β-Ethoxyethyl)-4-phenyl-6-nitro-1,2-dihydrothieno[2,3-d]pyrimidin-2-one 1-(β-Acetoxyethyl)-4-phenyl-6-nitro-1,2-dihydrothieno[2,3-d]pyrimidin-2-one 1-(Methoxycarbonylmethyl)-4-phenyl-6-nitro-1,2-dihydrothieno[2,3-d]pyrimidin-2-one 1-(N-Methylcarbamoylmethyl)-4-phenyl-6-nitro-1,2-dihydrothieno[2,3-d]pyrimidin-2-one 1-(Carbamoylethyl)-4-phenyl-6-nitro-1,2-dihydrothieno[2,3-d]pyrimidin-2-one 1-(β-Methylthioethyl)-4-phenyl-6-nitro-1,2-dihydrothieno[2,3-d]pyrimidin-2-one 1-Allyl-4-phenyl-6-nitro-1,2-dihydrothieno[2,3-d]pyrimidin-2-one 1-(β-Diethylaminoethyl)-4-phenyl-6-nitro-1,2-dihydrothieno[2,3-d]pyrimidin-2-one 1-(β-Pyrrolidinoethyl)-4-phenyl-6-nitro-1,2-dihydrothieno[2,3-d]pyrimidin-2-one 1-(β-Morpholinoethyl)-4-phenyl-6-nitro-1,2-dihydrothieno[2,3-d]pyrimidin-2-one 1-(β-Piperidinoethyl)-4-phenyl-6-nitro-1,2-dihydrothieno[2,3-d]pyrimidin-2-one The thienopyrimidine derivatives of the formulae [I], [II] and [III], which have not been described in any literature, have excellent uricosuric activity, with low toxicities to mammals which render them useful as synthetic medicinals. For example, the thienopyrimidine of the formula [I] has remarkably potent uricosuric activity, which has never reported in any literature. Details are as shown below.

Effect of uric acid excretion in mice

Mice of ddN strain, weighing 18 g to 20 g, were used. After the intravenous injection of 20 mg per kilogram of body weight of uric acid, they were given oral dose of test compounds in amount of 100 mg per kilogram of body weight. Urine of each group of mice, consisting of 4 animals each, was collected for 5 hours after the dosage and the concentration of uric acid in urine was determined by an enzymatic method (i.e. uricase method) employing ultraviolet spectrophotometry.

The results are shown in the Table.

Table

Effect on excretion of uric acid in mice

| Compounds | uric acid excretion (μg/100 g of body weight) |
|---|---|
| 1-Cyclopropylmethyl-4-phenyl-1,2-dihydrothieno[2,3-d]pyrimidin-2-one | 23.6±3.9 |
| 1-Methyl-4-phenyl-5-methyl-6-chloro-1,2-dihydrothieno[2,3-d]-pyrimidin-2-one | 39.2±8.2 |
| 1-Methyl-4-(o-fluorophenyl)-6-methyl-1,2-dihydrothieno[2,3-d]-pyrimidin-2-one | 35 |
| 1-Methyl-4-(o-fluorophenyl)-1,2,5,6,7,8-hexahydrobenzothieno[2,3-d]pyrimidin-2-one | 38 |
| Probenecid | 16.9±2.2 |
| Non-medicated control | 8.3±1.4 |

As shown in the table, thienopyrimidine derivatives of the present invention show greater excretion of uric acid than the non-medicated control or probenecid, which is most widely used as a uricosuric agent in the world.

Thienopyrimidines of the present invention can be administered parenterally or orally in any of the usual therapeutic dosage forms with dosage adjusted to individual needs, that is, in solid or liquid dosage forms such as tablets, dragies, capsules, suspensions, solutions, elixirs and the like. The dosage of the present therapeutic agents may vary from 0.2 to 50 mg per kg of body weight per day with the form of administration and the particular compound chosen.

The invention is illustrated more particularly by way of the following examples, but, as will be more apparent, is not limited to the details thereof.

Starting materials are prepared by the following methods.

Method A. By the procedure described in Chemische Berichte vol. 98, page 3571 (1965), the following compounds are prepared.

2-Amino-3-(o-fluorobenzoyl)-thiophene, m.p. 145°–°146.5°C

2-Amino-3-benzoylthiophene, m.p. 152°–°153.5°C

2-Amino-3-(o-chlorobenzoyl)-thiophene, m.p. 137°–°139°C

2-Amino-3-benzoyl-4-methylthiophene, m.p. 148°–°150°C

2-Amino-3-(o-fluorobenzoyl)-4-methylthiophene, m.p. 163°–°164°C

2-Amino-3-(o-chlorobenzoyl)-4-methylthiophene, m.p. 143°–144°C

Method B. By the procedure described in Journal of Oganic Chemistry, Volume 32, page 2376 (1967), the following compounds are prepared.

2-Amino-3-(o-chlorobenzoyl)-5-ethylthiophene, m.p. 132.5°–133.5°C

2-Amino-3-(o-fluorobenzoyl)-5-methylthiophene, m.p. 168°–170°C

2-Amino-3-(o-fluorobenzoyl)-4,5,6,7-tetrahydrobenzo[b]thiophene, m.p. 175.5°–177.5°C 2-Amino-3-benzoyl-4,5,6,7-tetrahydrobenzo[b]thiophene, m.p. 152′–154°C

Example 1

A mixture of 17.85 g of 2-amino-3-(o-fluorobenzoyl)-5-methylthiophene, 25.69 g of ethyl carbamate and 1.55 g of zinc chloride is heated at 200°C for 30 minutes. After cooling, the reaction mixture is washed with chloroform, then with water, and filtered to give 4-(o-fluorophenyl)-6-methyl-1,2-dihydrothieno[2,3-d]pyrimidin-2-one as crystalline solids. Recrystallization from chloroform-ethanol gives crystals having a melting point of 282° – 284°C.

Example 2

To a solution of 12.4 g of 4-(o-fluorophenyl)-6-methyl-1,2-dihydrothieno[2,3-d]pyrimidin-2-one in 248 ml of dimethylformamide is added 2.58 g of 67% sodium hydride. After stirring at 50°C for 1 hour and cooling to room temperature, 20.45 g of methyl iodide in 61.4 ml of dimethylformamide is added dropwise thereto. The mixture is stirred at room temperature for 1 hour, then poured into water and extracted with chloroform. The chloroform extracts are washed with water, dried over sodium sulfate, and the solvent is removed under reduced pressure. The residue is chromatographed on silica gel using chloroform as an eluent to give 1-methyl-4-(o-fluorophenyl)-6-methyl-1,2-dihydrothieno[2,3-d]pyrimidin-2-one as crystals having a melting point of 119° – 121°C (after recrystallization from chloroform-ethanol), and 3-methyl-4-(o-fluorophenyl)-6-methyl-3H-thieno[2,3-d]pyrimidin-2-one as crystals having a melting point of 239° – 241°C.

Example 3

A mixture of 10.0 g of 2-amino-3-(o-chlorobenzoyl)-thiophene, 14.26 g of ethyl carbamate and 0.86 g of zinc chloride is heated at 200°C for 30 minutes. After cooling, the reaction mixture is well washed with chloroform, then with water, and filtered to give crude crystals of 4-(o-chlorophenyl)-1,2-dihydrothieno[2,3-d]pyrimidin-2-one.

Infrared absorption spectrum, $\gamma_{max}$ 1630 cm$^{-1}$ (C=O)

Example 4

To a solution of 4.0 g of 4-(o-chlorophenyl)-1,2-dihydrothieno[2,3-d]pyrimidin-2-one in 80 ml of dimethylformamide is added 0.82 g of 63% sodium hydride. The resulting mixture is stirred at room temperature for 30 minutes. Then, 6.48 g of methyl iodide in 33 ml of dimethylformamide is added dropwise thereto. The mixture is stirred for 2 hours at room temperature. The reaction mixture is poured into water and extracted with chloroform. The chloroform extracts are washed with water, dried over sodium sulfate, and the solvent is removed under reduced pressure. The residue is chromatographed on silica gel, using chloroform as an eluent. From the first fraction, 2-methoxy-4-(o-chlorophenyl)-thieno[2,3-d]pyrimidine is obtained as crystals having a melting point of 172.5° – 174.5°C (after recrystallization from ether). From the second fraction, 1-methyl-4-(o-chlorophenyl)-1,2-dihydrothieno[2,3-d]pyrimidin-2-one is obtained as crystals having a melting point of 225° – 226°C (after recrystallization from chloroform-ethanol). From the third fraction, 3-methyl-4-(o-chlorophenyl)-3H-thieno[2,3-d]pyrimidin-2-one is obtained as crystals having a melting point of 190° – 192°C (after recrystallization from ethanol-ether).

Example 5

To a solution of 450 mg of 1-methyl-4-(o-chlorophenyl)-1,2-dihydrothieno[2,3-d]pyrimidin-2-one in 11 ml of chloroform is added dropwise 0.66 g of sulfuryl chloride. After stirring the reaction mixture for 7 hours at 50°C, the reaction mixture is neutralized with aqueous ammonia, then extracted with chloroform. The chloroform extracts are washed with water, dried and evaporated under reduced pressure to a residue to give crystals, which are recrystallized from ethanol-ether to give 1-methyl-4-(o-chlorophenyl)-6-chloro-1,2-dihydrothieno[2,3-d]pyrimidin-2-one as crystals having a melting point of 164° – 166°C.

Example 6

A mixture of 500 mg of 2-amino-3-(o-fluorobenzoyl)thiophene, 760 mg of ethyl carbamate and 46 mg of zinc chloride is heated at 200°C for 1 hour. After cooling, the reaction mixture is washed with chloroform and filtered to give crystals, which are disolved in acetone and filtered. The filtrate is condensed under reduced pressure to give 4-(o-fluorophenyl)-1,2-dihydrothieno[2,3-d]pyrimidin-2-one as crystals having a melting point of 254° – 256°C. Recrystallization from acetone gives crystals having a melting point of 278° – 279°C (decomp.)

Example 7

To a solution of 9.49 g of 4-(o-fluorophenyl)-1,2-dihydrothieno[2,3-d]pyrimidin-2-one in 200 ml of dimethylformamide is added 1.76 g of 63% sodium hydride. The mixture is stirred at 60°C for 1 hour. The mixture is cooled to room temperature and 10.93 g of methyl iodide in 33 ml of dimethylformamide is added dropwise thereto. The mixture is stirred for 2 hours at room temperature. The reaction mixture is poured into water and extracted with chloroform. The chloroform extracts are washed with water, dried over sodium sulfate, and the solvent is removed under reduced pressure. The residue is chromatographed on silica gel, using chloroform as an eluent. From the first fraction, 2-methoxy-4-(o-fluorophenyl)-thieno[2,3-d]pyrimidine is obtained as crystals having a melting point of 175° – 176.5°C (after recrystallization from ethanol). From the second fraction, 1-methyl-4-(o-fluorophenyl)-1,2-dihydrothieno[2,3-d]pyrimidin-2-one is obtained as crystals having a melting point of 222° – 223°C (after recrystallization from ethanol). From the third fraction, 3-methyl-4-(o-fluorophenyl)-3H-thieno[2,3-d]pyrimidin-2-one is obtained as crystals having a melting point of 191° – 192.5°C (after recrystallization from ethanol).

Example 8

To a solution of 0.5 g of 1-methyl-4-(o-fluorophenyl)-1,2-dihydrothieno[2,3-d]pyrimidin-2-one in 20 ml of methylene chloride is added dropwise 1.21 g of sulfuryl chloride. After stirring the reaction mixture for 72 hours at room temperature, the reaction mixture is neutralized with aqueous ammonia, then extracted with methylene chloride. The methylene chloride extracts are washed with water, dried and evaporated under reduced pressure to a residue, to give crystals which are recrystallized from ethanol to give 1-methyl-4-(o-fluorophenyl)-6-chloro-1,2-dihydrothieno[2,3-d]pyrimidin-2-one as crystals having a melting point of 192.5° – 194°C.

Example 9

A mixture of 18.5 g of 2-amino-3-(o-fluorobenzoyl)-4-methylthiophene, 26.6 g of ethyl carbamate and 1.61 g of zinc chloride is heated at 200°C for 30 minutes. After cooling, the reaction mixture is washed with chloroform, then with water, and filtered to give crude crystals of 4-(o-fluorophenyl)-5-methyl-1,2-dihydrothieno[2,3-d]pyrimidin-2-one having a melting point of 258° – 261°C.

Example 10

To a solution of 13.57 g of 4-(o-fluorophenyl)-5-methyl-1,2-dihydrothieno[2,3-d]pyrimidin-2-one in 271 ml of dimethylformamide is added 2.8 g of 63% sodium hydride. The mixture is stirred at room temperature for 1 hour. Then, 22.15 g of methyl iodide in 66 ml of dimethylformamide is added dropwise thereto. The mixture is stirred for 2 hours at room temperature. The reaction mixture is poured into water and extracted with chloroform. The chloroform extracts are washed with water, dried over sodium sulfate, and the solvent is removed under reduced pressure. The residue is chromatographed on silica gel, using chloroform as an eluent. From the first fraction, 2-methoxy-4-(o-fluorophenyl)-5-methyl-thieno[2,3-d]pyrimidine is obtained as crystals having a melting point of 177° – 179°C. From the second fraction, 1-methyl-4-(o-fluorophenyl)-5-methyl-1,2-dihydrotheino[2,3-d]pyrimidin-2-one is obtained as crystals having a melting point of 275° – 277°C. From the the third fraction, 3-methyl-4-(o-fluorophenyl)-5-methyl-3H-thieno[2,3-d]pyrimidin-2-one is obtained as crystals having a melting point of 176° – 178°C.

Example 11

To a solution of 500 mg of 1-methyl-4-(o-fluorophenyl)-5-methyl-1,2-dihydrothieno[2,3-d]pyrimidin-2-one in 15 ml of glacial acetic acid is added 295 mg of sulfuryl chloride in 3 ml of glacial acetic acid at 40°C. After stirring the reaction mixture for 19 hours at room temperature, the reaction mixture is neutralized with aqueous ammonia under cooling, then extracted with chloroform. The chloroform extracts are washed with water, dried, and evaporated under reduced pressure to a residue to give crystals of 1-methyl-4-(o-fluorophenyl)-5-methyl-6-chloro-1,2-dihydrothieno[2,3-d]pyrimidin-2-one, which are recrystallized from ethanol-ether to give crystals having a melting point of 175° – 176°C.

Example 12

A mixture of 20.0 g of 2-amino-3-(o-fluorobenzoyl)-4,5,6,7-tetrahydrothiophene, 24.6 g of ethyl carbamate and 1.49 g of zinc chloride is heated at 200°C for 1 hour. After cooling, the reaction mixture is washed with chloroform and filtered to give a solid, which is washed with water to give 18.1 g of 4-(o-fluorophenyl)-1,2,5,6,7,8-hexahydrobenzothieno[2,3-d]pyrimidin-2-one as crystals. Recrystallization from chloroform-ethanol gives crystals having a melting point of 274° – 277°C.

Example 13

To a solution of 16.1 g of 4-(o-fluorophenyl)-1,2,5,6,7,8-hexahydrobenzothieno[2,3-d]pyrimidin-2-one in 322 of dimethylformamide is added 2.88 g of 67% sodium hydride. The mixture is stirred for 1 hour at room temperature, and 22.83 g of methyl iodide in 68 ml of dimethylformamide is added thereto at 10°C. The resulting reaction mixture is stirred for 2 hours at room temperature, then poured into water and extracted with chloroform. The chloroform extracts are washed with water, dried over sodium sulfate, and the solvent is removed under reduced pressure. The residue is chromatographed on silica gel, using chloroform as an eluent. From the first fraction 2-methoxy-4-(o-fluorophenyl)-5,6,7,8-tetrahydrobenzothieno[2,3-d]pyrimidine is obtained as crystals having a melting point of 98° – 100°C. From the second fraction, 1-methyl-4-(o-fluorophenyl)-1,2,5,6,7,8-hexahydrobenzothieno[2,3-d]pyrimidin-2-one is obtained as crystals having a melting point of 221° – 222.5°C.

Example 14

A mixture of 10.0 g of 2-amino-3-benzoylthiophene, 16.57 g of ethyl carbamate and 1.00 g of zinc chloride is heated at 200°C for 1 hour. After cooling, the reaction mixture is washed with chloroform, then with water, and filtered to give a solid of 4-phenyl-1,2-dihydrothieno[2,3-d]pyrimidin-2-one. Recrystallization from a mixture of ethanol and dimethylformamide gives crystals having a melting point of 247° – 249°C.

Example 15

To a solution of 4.0 g of 4-phenyl-1,2-dihydrothieno[2,3-d]pyrimidin-2-one in 80 ml of dimethylformamide is added 0.8 g of 63% sodium hydride. The mixture is stirred at 60°C for 1 hour. The mixture is cooled to room temperature and 4.97 g of methyl iodide in 15 ml of dimethylformamide is added dropwise thereto at 10°C. The mixture is stirred for 2 hours at room temperature. The reaction mixture is poured into water and extracted with chloroform. The chloroform extracts are washed with water, dried over sodium sulfate, and the solvent is removed under reduced pressure. The residue is chromatographed on silica gel, using chloroform as an eluent. From the first fraction, 2-methoxy-4-phenylthieno[2,3-d]pyrimidine is obtained as crystals having a melting point of 160° – 161.5°C (after recrystallization from ethanol). From the second fraction, 1-methyl-4-phenyl-1,2-dihydrothieno[2,3-d]pyrimidin-2-one is obtained as crystals having a melting point of 256° – 257.5°C (after recrystallization from ethanol). From the third fraction, 3-methyl-4-phenyl-3H-thieno[2,3-d]pyrimidin-2-one is obtained as crystal having a melting point of 175° – 181°C (after recrystallization from ethanol).

Example 16

To a solution of 0.77 g of 1-methyl-4-phenyl-1,2,-dihydrothieno[2,3,-d]pyrimidin-2-one in 70 ml of methylene chloride is added dropwise 0.77 g of sulfuryl chloride. After stirring the reaction mixture for 72 hours at room temperature, the reaction mixture is neutralized with aqueous ammonia, then extracted with methylene chloride. The methylene chloride extracts are washed with water, dried and evaporated under reduced pressure to a residue, to give crystals which are recrystallized from ethanol to give 1-methyl-4-phenyl-6-chloro-1,2-dihydrothieno[2,3-d]pyrimidin-2-one as prisms having a melting point of 136° – 140°C.

Example 17

To a solution of 500 mg of 4-phenyl-1,2-dihydrothieno[2,3-d]pyrimidin-2-one in 10 ml of dimethylformamide is added 100 mg of 63% sodium hydride. After stirring at 60°C for 1 hour, 590 mg of cyclopropylmethyl bromide is added dropwise thereto. The mixture is heated at 120°C for 4 hours, then cooled to room temperature. The reaction mixture is poured into water and extracted with chloroform. The chloroform extracts are washed with water, dried over sodium sulfate, and the solvent is removed under reduced pressure. The residue is chromatographed on silica gel, using chloroform as an eluent. From the first fraction, 2-(cyclopropylmethoxy)-4-phenylthieno[2,3-d]pyrimidine is obtained as crystals having a melting point of 86.5°– 87.5°C. From the second fraction 1-cyclopropylmethyl-4-phenyl-1,2-dihydrothieno[2,3-d]pyrimidin-2-one is obtained as crystals having a melting point of 191° – 191.5°C.

Example 18

To a solution of 0.80 g of 1-cyclopropylmethyl-4-phenyl-1,2-dihydrotheino[2,3-d]pyrimidin-2-one in 16 ml of dichloromethane is added dropwise 0.687 g of sulfuryl chloride in 3.4 ml of dichloromethane at room temperature. After stirring the reaction mixture for 48 hours at room temperature, the resulting reaction mixture is neutralized with aqueous ammonia, then extracted with methylene chloride. The methylene chloride extracts are washed with water, dried over sodium sulfate and evaporated under reduced pressure to give crystals, which are recrystallized from ethanol to give 1-cyclopropylmethyl-4-phenyl-6-chloro-1,2-dihydrothieno[2,3-d]pyrimidin-2one as crystals having a melting point of 149° – 151°C.

Example 19

To a suspension of 380 mg of 1-cyclopropylmethyl-4-phenyl-1,2-dihydrothieno[2,3-d]pyrimidin-2-one and 1.2 ml of acetic anhydride is added 380 mg of fuming nitric acid (d = 1.50) is 1.20 ml of acetic anhydride. The reaction mixture is stirred for 48 hours at room temperature, then neutralized with aqueous ammonia under ice-cooling and extracted with chloroform. The chloroform extracts are washed with water, dried over sodium sulfate and evaporated under reduced pressure to give crystals, which are recrystallized from chloroform-ethanol to give 1-cyclopropylmethyl-4-phenyl-6-nitro-1,2-dihydrothieno[2,3-d]pyrimidin-2-one as crystals having a melting point of 216° – 218°C.

Example 20

A mixture of 2.0 g of 2-methylamino-3-benzoyl-4-methylthiophene, 2.3 g of ethyl carbamate and 0.18 g of zinc chloride is heated at 200°C for 1 hour. After cooling, the reaction mixture is extracted with chloroform. The extracts are combined, washed with water, dried over sodium sulfate and concentrated to dryness under reduced pressure. The residue is recrystallized from chloroform-ethanol to give 1-methyl-4-phenyl-5-methyl-1,2-dihydrothieno[2,3-d]pyrimidin-2-one as crystals having a melting point of 275° – 280°C.

The starting materials of the present invention are prepared as follows.

Example 20-a

To a mixture of 4.50 g of 2-amino-3-benzoyl-4-methylthiophene, 4.5 g of pyridine and 450 ml of anhydrous ether is added dropwise 4.50 g of acetyl chloride. Then the reaction mixture is stirred under reflux for 5 hours. After cooling, the reaction mixture is poured into water. The ether layer is separated and washed with water, and dried over sodium sulfate. The solvent is removed under reduced pressure to give an oily residue, which is crystallized from ether to give 2-acetylamino-3-benzoyl-4-methylthiophene having a melting point of 106° – 107°C.

Example 20-b

To a solution of 1.0 g of 2-acetylamino-3-benzoyl-4-methylthiophene in 20 ml of dimethylformamide is added 0.207 g of 63% sodium hydride. The mixture is stirred at room temperature for 30 minutes. Then 1.64 g of methyl iodide in 4.9 ml of dimethylformaide is added thereto. The mixture is stirred at room temperature for 3 hours, then poured into water, and extracted with benzene. The benzene extracts are washed with water, dried over sodium sulfate, and the solvent is removed under reduced pressure to give crystals, which are recrystallized from ether to give N-methyl-2-acetylamino-3-benzoyl-4-methylthiophene as crystals having a melting point of 121.5° – 122.5°C.

Example 20-c

To a solution of 400 mg of N-methyl-2-acetylamino-3-benzoyl-4-methylthiophene in 8 ml of ethanol, is added 0.11 g of potassium hydroxide in 2.9 ml of water. The mixture is heated at 95°C for 30 minutes, evaporated under reduced pressure to a residue. Water is added to the residue and the resulting mixture is extracted with dichloromethane. The dichloromethane extracts are washed with water, dried over sodium sulfate and then evaporated under reduced pressure to give crystals, which are recrystallized from ethanol-ether to give 2-methylamino-3-benzoyl-4-methylthiophene as crystals having a melting point of 144° – 145°C.

Example 21

To a solution of 1.33 g of 1-methyl-4-phenyl-5-methyl-1,2-dihyrothieno[2,3-d]-pyrimidin-2-one in 35 of chloroform is added dropwise 1.62 g of sulfuryl chloride in 6 ml of chloroform. After stirring the reaction mixture for 5 hours at room temperature, the reaction mixture is neutralized with aqueous ammonia and then extracted with chloroform. The chloroform extracts are washed with water, dried, evaporated under reduced pressure to a residue to give crystals of 1-methyl-4-phenyl-5-methyl-6-chloro-1,2-dihydrothieno[2,3-d]pyrimidin-2-one, which are recrystallized from ethanol-ether to give crystals having a melting point of 190° – 191.5°C.

Example 22

A mixture of 1.5 g of 2-methylamino-3-benzoyl-4,5,6,7-tetrahydrobenzo[b]thiophene, 1.5 g of ethyl carbamate and 0.11 g of zinc chloride is heated at 200°C for 1 hour. After cooling, the reaction mixture is extracted with chloroform. The chloroform extracts are combined, washed with water, dried over sodium sulfate and concentrated to dryness under reduced pressure and residue is recrystallized from ethanol to give 1-methyl-4-phenyl-1,2,5,6,7,8-hexahydrobenzothieno[2,3-d]pyrimidin-2-one as crystals having a melting point of 215° – 216°C.

The starting materials are prepared as follows.

Example 22-a

To a mixture of 35 g of 2-amino-3-benzoyl-4,5,6,7-tetrahydrobenzo[b]thiophene, 35 g of pyridine and 1950 ml of anhydrous ether is added dropwise 35 g of acetyl chloride. Then the reaction mixture is stirred under reflux for 3 hours. After cooling, the reaction mixture is poured into water. The ether layer is separated and washed with water, and dried over sodium sulfate. The solvent is removed under reduced pressure to give an oily residue, which is crystallized from ether to give 2-acetylamino-3-benzoyl-4,5,6,7-tetrahydrobenzo[b]thiophene having a melting point of 116°–119°C.

Example 22-b

To a solution of 5.0 g of 2-acetylamino-3-benzoyl-4,5,6,7-tetrahydrobenzo[b]thiophene in 60 ml of dimethylformamide is added 0.9 g of 63% sodium hydride. The mixture is stirred at room temperature for 30 minutes. Then 71.3 g of methyl iodide in 20 ml of dimethylformamide is added thereto. The mixture is stirred at room temperature for 3 hours, then poured into water, and extracted with benzene. The benzene extracts are washed with water, dried over sodium sulfate, and the solvent is removed under reduced pressure to give 2-(N-methylacetylamino)-3-benzoyl-4,5,6,7-tetrahydrobenzo[b]thiophene as an oil. This layer chromatography (Kiesel gel) shows the $R_f$ value of 0.44 using a mixture of ethyl acetate and chloroform (1 : 1 V/V).

Example 22-c

To solution of 5.0 g of N-methyl-2-acetylamino-3-benzoyl-4,5,6,7-tetrahydrobenzo[b]thiophene in 120 ml of ethanol, is added 2.7 g of potassium hydroxide in 60 ml of water. The mixture is heated at 95°C for 4 hours, evaporated under reduced pressure to a residue. Water is added to the residue and extracted with chloroform. The chloroform extracts are washed with water, dried over sodium sulfate, then evaporated under reduced pressure to give crystals, which are recrystallized from ethanol to give 2-methylamino-3-benzoyl-4,5,6,7-tetrahydrobenzo[b]thiophene as crystals having a melting point of 127.5° - 129.5°C.

Example 23

A mixture of 0.59 g of 2-methylamino-3-propionylthiophene, 1.18 g of ethyl carbamate and 0.07 g of zinc chloride is heated at 200°C for 1 hour. After cooling, the reaction mixture is extracted with chloroform. The extracts are combined, washed with water, dried over sodium sulfate and concentrated to dryness under reduced pressure. The residue is chromatographed on silica gel using chloroform as an eluent to give 1-methyl-4-ethyl-1,2-dihydrothieno[2,3-d]pyrimidin-2-one as crystals having a melting point of 155.5°–156.5°C (after recrystallization from ethanol).

The starting materials are prepared as follows.

Example 23-a

To a solution of 1.80 g of 2-acetylamino-3-pripionylthiophene in 18 ml of dimethylformamide is added 0.418 g of 63% sodium hydride. The mixture is stirred at room temperature for 30 minutes. Then 3.89 g of methyl iodide in 2 ml of dimethylformamide is added thereto. The mixture is stirred at room temperature for 2 hours, then poured into water, and extracted with benzene. The benzene extracts are washed with water, dried over sodium sulfate, and the solvent is removed under reduced pressure to give crystals which are recrystallized from ether to give N-methyl-2-acetylamino-3-propionylthiophene as crystals having a melting point of 78.5°–79.5°C.

Example 23-b

To a solution of 1.255 g of N-methyl-2-acetylamino-3-propionylthiophene in 25 ml of ethanol, is added 0.45 g of potassium hydroxide in 10 ml of water. The mixture is heated at 95°C for 1 hour, evaporated under reduced pressure to a residue. Water is added to the residue and extracted with dichloromethane. The dichloromethane extracts are washed with water, dried over sodium sulfate, then evaporated under reduced pressure to give an oil. The residual oil is chromatographed on silica gel, using chloroform as an eluent to give 2-methylamino-3-propionylthiophene as an oil.

$IR_{oil}^{cm-1}$ 3300, 1615

Example 24

A mixture of 11.7 g of 2-methylamino-3-(o-chlorobenzoyl)-5-ethylthiophene, 11.18 g of ethyl carbamate and 0.86 g of zinc chloride is heated at 200°C for 1 hour. After cooling, the reaction mixture is extracted with chloroform. The extracts are combined, washed with water, dried over sodium sulfate and contentrated to dryness under reduced pressure. The residue is chromatographed on silica gel using chloroform as an eluent to give 1-methyl-4-(o-chlorophenyl)-6-ethyl-1,2-dihydrothieno[2,3-d]pyrimidin-2-one as crystals having a melting point of 99°–χ°C (after recrystallization from isopropanol).

The starting materials are prepared as follows.

Example 24-a

To a mixture of 46.4 g of 2-amino-3-(o-chlorobenzoyl)-5-ethylthiophene, 46.4 g of pyridine and 1160 ml of anhydrous ether is added dropwise 46.4 g of acetyl chloride. Then the reaction mixture is stirred under reflux for 2 hours. After cooling, the reaction mixture is poured into water. The ether layer is separated and washed with water, and dried over sodium sulfate. The solvent is removed under reduced pressure to give crystals of 2-acetylamino-3-(o-chlorobenzoyl)-5-ethylthiophene, which are recrystallized from ethanol-ether to give crystals having a melting point of 132° – 134°C; yield 42.44 g (79%).

Example 24-b

To a solution of 36.44 g of 2-acetylamino-3-(o-chlorobenzoyl)-5-ethylthiohene in 729 ml of dimethylformamide is added 6.36 g of 63% sodium hydride. The mixture is stirred at room temperature for 30 minutes, then 50.44 g of methyl iodide in 151 ml of dimethylformamide is added thereto. The mixture is stirred at room temperature for 2 hours, then poured into water, and extracted with benzene. The benzene extracts are washed with water, dried over sodium sulfate, and the solvent is removed under reduced pressure to give 2-(N-methylacetylamino)-3-(o-chlorobenzoyl)-5-ethylthiophene as an oil.

$IR_{oil}^{cm-1}$ 1670, 1590, 1540

Example 24-c

To a solution of 26.0 g of 2-(N-methylacetylamino)-3-(o-chlorobenzoyl)-5-ethylthiophene in 520 ml of ethanol, is added 5.85 g of potassium hydroxide in 164 ml of water. The mixture is heated at 95°C for 1 hour, then evaporated under reduced pressure to a residue. Water is added to the residue and extracted with dichloromethane. The dichloromethane extracts are washed with water, dried over sodium sulfate, then evaporated under reduced pressure to give crystals, which are chromatographed on silica gel using chloroform as an eluent to give 15.26 g of 2-(N-methylamino)-3-(o-chlorobenzoyl)-5-ethylthiophene as crystals having a melting point of 100° – 102°C (after recrystallization from ether); yield 67.5%.

Example 25

A mixture of 700 mg of 2-methylamino-3-(o-fluorobenzoyl)-5-chlorothiophene, 700 mg of ethyl carbamate and 50 mg of zinc chloride is heated at 200°C for 1 hour. After cooling, the reaction mixture is extracted with chloroform. The extracts are combined, washed with water, dried over sodium sulfate and concentrated under reduced pressure to give a residue, which is chromatographed on silica gel using chloroform as an eluent to give crystals of 1-methyl-4-(o-fluorophenyl)-6-chloro-1,2-dihydrothieno[2,3-d]pyrimidin-2-one as crystals having a melting point of 192° – 194°C (after recrystallization from ethanol).

The starting materials are prepared as follows.

Example 25-a

To a solution of 2.50 g of 2-(N-methylacetylamino)-3-(o-fluorobenzoyl)thiophene in 50 ml of dichloromethane is added dropwise 2.16 g of sulfuryl chloride in 30 ml of dichloromethane. After stirring the reaction mixture for overnight at room temperature, the reaction mixture is neutralized with aqueous ammonia, then extracted with methylene chloride. The methylene chloride extracts are washed with water, dried over sodium sulfate, then evaporated under reduced pressure to a residue. The residue is chromatographed on silica gel using chloroform as an eluent to give 2-(N-methylacetylamino)-3-(o-fluorobenzoyl)-5-chlorothiophene as an oil.

$IR_{oil}^{cm^{-1}}$ 1670, 1600, 1580, 1530.

Example 25-b

To a solution of 1.5 g of 2-(N-methylacetylamino)-3-(o-fluorobenzoyl)-5-chlorothiophene in 7 ml of ethanol is added 4 ml of 6 N aqueous hydrochloric acid. The mixture is heated at 90°C for 2 hours, evaporated under reduced pressure to a residue, neutralized with aqueous ammonia, then extracted with ether. The ether extracts are washed with water, dried over sodium sulfate, when evaporated under reduced pressure to a oil, which is chromatographed on silica gel using chloroform as an eluent to give 2-(N-methylamino)-3-(o-fluorobenzoyl)-5-chlorothiophene as crystals having a melting point of 93° – 94°C.

Example 26

A mixture of 500 mg of 2-methylamino-3-(o-fluorobenzoyl)thiophene, 716 mg of ethyl carbamate and 44 mg of zinc chloride is heated at 200°C for 1 hour. After cooling, the reaction mixture is extracted with chloroform. The extracts are combined, washed with water, dried over sodium sulfate and concentrated to dryness under reduced pressure and, the residue is recrystallized from ethanol to give 1-methyl-4-(o-fluorophenyl)-1,2-dihyrothieno[2,3-d]pyrimidin-2-one as crystals having a melting point of 221.5° – 222°C.

The starting materials are prepared as follows.

Example 26-a

To a mixture of 3.90 g of 2-amino-3-(o-fluorobenzoyl)thiophene, 3.90 g of pyridine and 170 ml of anhydrous ether is added dropwise 3.90 g of acetyl chloride. Then the reaction mixture is stirred under reflux for 7 hours. After cooling, the reaction mixture is poured into water. The ether layer is separated and washed with water, and dried over sodium sulfate. The solvent is removed under reduced pressure to give an oily residure, which is crystallized from ether to give 2-acetylamino-3-(o-fluorobenzoyl)thiophene having a melting point of 143.5° – 144.5°C.

Example 26-b

To a solution of 1.0 g of 2-acetylamino-3-(o-fluorobenzoyl)thiophene in 10 ml of dimethylformamide is added 0.220 g of 63 % sodium hydride. The mixture is stirred at room temperature for 30 minutes. Then 1.0 g of methyl iodide in 1 ml of dimethylformamide is added thereto. The mixture is stirred at room temperature overnight, then poured into water, and extracted with benzene. The benzene extracts are washed with water, dried over sodium sulfate, and the solvent is removed under reduced pressure. The residual oil is chromatographed on silica gel, using chloroform as an eluent to give crystals, which are recrystallized from ether to give N-methyl-1-acetylamino-3-(o-fluorobenzoyl)thiophene as crystals having a melting point of 94° – 95°C.

Example 26-c

To a solution of 2.5 g of N-methyl-2-acetylamino-3-(o-fluorobenzoyl)thiophene in 12.5 ml of ethanol, is added 6.6 ml of 6 N aqueous hydrochloric acid. The mixture is heated at 90°C for 3 hours. After cooling, the reaction mixture is neutralized with aqueous ammonia, then extracted with ether. The ether extracts are washed with water, dried over sodium sulfate, then evaporated under reduced pressure to give an oil, which is crystallized from ethanol to give 2-methylamino-3-(o-fluorobenzoyl)thiophene as crystals having a melting point of 184.5° – 186°C.

Example 27

To a suspension of 1.5 g of 1-methyl-4-phenyl-1,2-dihydrothieno[2,3-d]pyrimidin-2-one and 6 ml of acetic anhydride is added 1.56 g of fuming nitric acid ($d = 1.50$) in 4.68 ml of acetic anhydride. After stirring at room temperature overnight, additional 1.56 g of fuming nitric acid ($d = 1.50$) in 6 ml of acetic anhydride is added at 50°C, then strong exothermic reaction occurs and the reaction temperature is reached to 70°C at maximum. After stirring the reaction mixture for 2 hours at 50°C, the reaction solution is poured into ice water, then neutralized with aqueous ammonia under ice cooling and extracted with chloroform. The chloroform extracts are washed with water, dried over sodium sulfate, and evaporated under reduced pressure to give crystals, which are recrystallized from chloroform-ethanol to give 1-methyl-4-phenyl-6-nitro-1,2-dihydrothieno[2,3-i d]pyrimidin-2-one as crystals having a melting point of 272° – 274°C.

Example 28

A mixture of 16.0 g of 2-methylamino-3-(o-chlorobenzoyl)-4-methylthiophene, 16.1 g of ethyl carbamate and 1.22 g of zinc chloride is heated at 200°C for 1 hour. After cooling, the reaction mixture is extracted with chloroform. The extracts are combined, washed with water, dried over sodium sulfate and concentrated to dryness under reduced pressure. The residue is chromatographed on silica gel using chloroform as an eluent to give 1-methyl-4-(o-chlorophenyl)-5-methyl-1,2-dihydrothieno[2,3-$d$]pyrimidin-2-one as crystals having a melting point of 267.5° – 268.5°C (after recrystallization from chloroformethanol).

The starting materials are prepared as follows.

Example 28-a

To a mixture of 62 g of 2-amino-(o-chlorobenzoyl)-4-methylthiophene, 62 g of pyridine and 2170 ml of anhydrous ether is added dropwise 62 g of acetyl chloride. The the reaction mixture is stirred under reflux for 4 hours and 30 minutes. After cooling, the reaction mixture is poured into water. The ether layer is separated and washed with water, and dried over sodium sulfate. The solvent is removed under reduced pressure to give an oily residue, which is crystallized from ethanol to give 2-acetylamino-3-(o-chlorobenzoyl)-4-methylthiophene having a melting point of 148° – 149°C.

Example 28-b

To a solution of 40.0 g of 2-acetylamino-3-(o-chlorobenzoyl)-4-methylthiophene in 800 ml of dimethylformamide is added 7.74 g of 63 % sodium hydride. The mixture is stirred at room temperature for 30 minutes. Then 61.34 g of methyl iodide in 184 ml of dimethylformamide is added thereto. The mixture is stirred at room temperature for 2 hours, then poured into water, and extracted with benzene. The benzene extracts are washed with water, dried over sodium sulfate, and the solvent is removed under reduced pressure. The residual oil is chromatographed on silica gel, using chloroform as an eluent to give 2-(N-methylacetylamino)-3-(o-chlorobenzoyl)-4-methylthiophene as an oil.

IR$_{oil}^{cm^{-1}}$ 3050, 1670, 1585, 1540

Example 28-c

To a solution of 29.6 g of 2-(N-methylacetylamino)-3-(o-chlorobenzoyl)-4-methylthiophene in 592 ml of ethanol, is added 6.97 g of potassium hydroxide in 190 ml of water. The mixture is heated at 95°C for 1 hour, evaporated under reduced pressure to a residue. Water is added to the residue and extracted with chloroform. The chloroform extracts are washed with water, dried over sodium sulfate, then evaporated under reduced pressure to give an oil. The residual oil is chromatographed on silica gel, using chloroform as an eluent to give 2-methylamino-3-(o-chlorobenzoyl)-4-methylthiophene as crystals having a melting point of 132° – 134°C (after recrystallization from ethanol).

Example 29

To a solution of 1.5 g of 1-methyl-4-(o-chlorophenyl)-5-methyl-1,2-dihydrothieno[2,3-$d$]pyrimidin-2-one in 30 ml of chloroform is added dropwise 1.62 g of sulfuryl chloride in 6 ml of chloroform. After stirring the reaction mixture for 2 hours at room temperature, the reaction mixture is neutralized with aqueous ammonia, then extracted with chloroform. The chloroform extracts are washed with water, dried, evaporated under reduced pressure to a residue to give crystals of 1-methyl-4-(o-chlorophenyl)-5-methyl-6-chloro-1,2-dihydrothieno[2,3-$d$]pyrimidin-2-one, which are recrystallized from ethanol to give 1.252 g of crystals having a melting point of 199.5° – 200.5°C; yield 74.5 %.

Example 30

A mixture of 4.0 g of 2-amino-3-propionylthiophene, 8.9 g of ethyl carbamate and 0.53 g of zinc chloride is heated at 200°C for 1 hour. After cooling, the resulting material is treated with hot water and then filtered. The filtrate is extracted with chloroform and the insoluble matter is washed with hot chloroform. The chloroform extracts were combined and washed with water. After removing the chloroform by distillation under reduced pressure, the resulting residue is crystallized from ethanol to give 4-ethyl-1,2-dihydrothieno[2,3-$d$]pyrimidine-2-one. Recrystallized from a mixture of ethanol and chloroform, there are obtained crystals having a melting point of 217° – 220°C.

The starting material was synthesized as follows.

Example 30-a

To a suspension of 21.9 g of 2-methyl-4H-thieno[2,3-$d$]-1,3-oxazin-4-one in 500 ml of dry ether, a Grignard solution prepared from 24.3 g of ethyl bromide, 4.77 g of metallic magnesium and 110 ml of ether is added dropwise at 15° – 20°C. The resulting mixture is stirred at room temperature overnight. To the reaction mixture, 500 ml of ice water is added with cooling and 120 ml of concentrated hydrochloric acid is added dropwise. After separating the mixture, the ether layer is neutralized with 28 % ammonia water and condensed under reduced pressure. The resulting residue is treated by a chromatographic method using silica gel and chloroform to give 2-acetamide-3-propionylthiophene of colorless prisms. Recrystallized from ether, there are obtained colorless prisms having a melting point of 73.5° – 74.0°C.

Example 30-b

A mixture of 2.43 g of 2-acetamide-3-propionylthiophene, 0.84 g of potassium hydroxide, 50 ml of ethanol and 20 ml of water is heated at 95°C for 10 minutes and then evaporated to dryness under reduced pressure. The residue is partitioned between water and dichloromethane. The dichloromethane layer is washed with water and evaporated to dryness to give 2-amino-3-propionylthiophene as crystals. Recrystallization from ether gives colorless prisms having a melting point of 140° – 142°C.

What is claimed is:

1. A thienopyrimidine derivative of the formula,

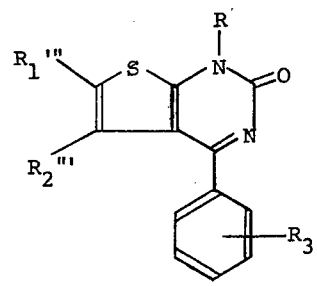

wherein R is methyl, cyclopropylmethyl, β-ethoxyethyl, β-acetoxyethyl, methoxycarbonylethyl, β-methoxythioethyl or allyl; $R_3$ is hydrogen, halogen, methyl or nitro; and $R_1'''$ and $R_2'''$ together form tetramethylene.

2. A thienopyrimidine derivative of the formula,

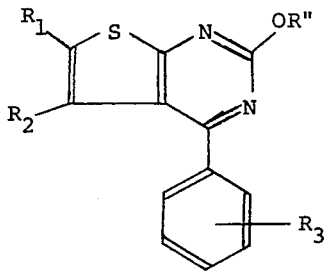

[II']

wherein $R_1$ is hydrogen, methyl, ethyl, halogen or nitro; $R_2$ is hydrogen or methyl; and $R_1$ and $R_2$ may form tetramethylene; $R_3$ is hydrogen, halogen, methyl or nitro; and R'' is methyl, cyclopropylmethyl, β-ethoxyethyl, β-acetoxyethyl, methoxycarbonylmethyl, β-methylthioethyl or allyl.

3. A thienopyrimidine derivative of the formula,

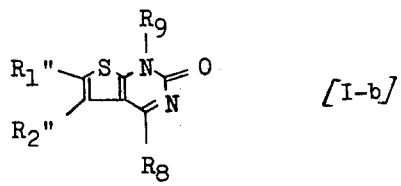

[I-b]

wherein $R_1''$, $R_2''$, $R_8$ and $R_9$ are independently hydrogen, methyl or ethyl.

4. A thienopyrimidine derivative of the formula,

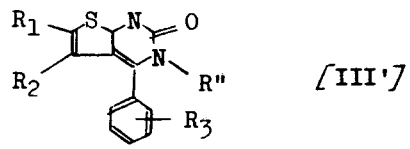

[III']

wherein $R_1$, $R_2$, $R_3$ and R'' are as defined in claim 2.

5. 1-Methyl-4-(o-fluorophenyl)-1,2,5,6,7,8-hexahydrobenzothieno[2,3-d]pyrimidin-2-one.

* * * * *